United States Patent
Rubinsztajn et al.

(10) Patent No.: US 7,148,370 B1
(45) Date of Patent: Dec. 12, 2006

(54) PROCESS FOR SYNTHESIS OF DIORGANOSILANES BY DISPROPORTIONATION OF HYDRIDOSILOXANES

(75) Inventors: Slawomir Rubinsztajn, Niskayuna, NY (US); James Anthony Cella, Clifton Park, NY (US); Julian Chojnowski, Lodz (PL); Witold Fortuniak, Lodz (PL); Jan Kurjata, Lodz (PL)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/185,466

(22) Filed: Jul. 20, 2005

(51) Int. Cl.
*C07F 7/18* (2006.01)
*C07F 7/08* (2006.01)

(52) U.S. Cl. .................. 556/469; 556/450; 556/451; 556/460; 556/462; 556/465; 556/466; 556/467

(58) Field of Classification Search ............... 556/450, 556/451, 460, 462, 465, 466, 467, 469
See application file for complete search history.

(56) References Cited

U.S. PATENT DOCUMENTS

| 2,731,485 A | 1/1956 | Wagner et al. |
| 5,767,216 A | 6/1998 | Frances et al. |
| 6,743,883 B1 | 6/2004 | Frances et al. |
| 2004/0127668 A1 | 7/2004 | Rubinsztajn et al. |

FOREIGN PATENT DOCUMENTS

| WO | WO 01/74938 | 10/2001 |
| WO | WO 02/12386 | 2/2002 |

OTHER PUBLICATIONS

Vladimir Gevorgyan et al., "*A Novel B($C_6F_5$)$_3$-Catalyzed Reduction of Alcohols and Cleavage of Aryl and Alkyl Ethers With Hydrosilanes*", American Chemical Society, Journal of Organic Chemistry, vol. 65, pp. 6179-6186, 2000.

Michael Rubin et al., "*Highly Efficient B($C_6F_5$)$_3$-Catalyzed Hydrosilylation of Olefins*", American Chemical Society, Journal of Organic Chemistry, vol. 67, pp. 1936-1940, 2002.

Daniel J. Parks et al., "*Tris(pentafluorophenyl)boron-Catalyzed Hydrosilation of Aromatic Aldehydes, Ketones, and Esters*", American Chemical Society, Journal of Organic Chemistry, vol. 118, pp. 9440-9441, 1996.

Slawomir Rubinsztajn et al., *Reaction of Siloxane Bonds via New Condensation Process*, Polymer Preprints, vol. 45(1), pp. 635-636, 2004.

Kirk Othmer's Encyclopedia of Chemical Technology, 3rd Edition, vol. 22, "*Silicon Compounds (Silanes)*", pp. 38-61, 1998.

Jim Cella et al., "*Polymerization reactions Mediated by Tris-Pentafluorophenyl Boron*", Abstracts, The 39th IUPAC Congress and the 86th Conference of the Canadian Society for Chemistry, Aug. 10-15, 2003, Ottawa, Canada.

Michael Rubin et al., "*B($C_6F_5$)$_3$-Catalyzed Allylation of Secondary Benzyl Acetates With Allylsilanes*", American Chemical Society, Organic Letters, vol. 3, No. 17, pp. 2705-2707, 2001.

Vladimir Gevorgyan et al., "*A Direct Reduction of Aliphatic Aldehyde, Acyl Chloride, Ester, and Carboxylic Functions Into a Methyl Group*", American Chemical Society, Journal of Organic Chemistry, vol. 66, pp. 1672-1675, 2001.

Daniel J. Parks et al., "*Studies On the Mechanism of B($C_6F_5$)$_3$-Catalyzed Hydrosilation of Carbonyl Functions*", American Chemical Society, Journal of Organic Chemistry, vol. 65, pp. 3090-3098, 2000.

James M. Blackwell et al., "*B($C_6F_5$)$_3$-Catalyzed Silation of Alcohols: A Mild, General Method for Synthesis of Silyl Ethers*", American Chemical Society, Journal of Organic Chemistry, vol. 64, pp. 4887-4892, 1999.

S. Rubinsztajn et al., "*New Rearrangement process Involving Cleavage of Siloxane Bond and Formation of Dimethylsilane*", Polymer Preprints, vol. 46, pp. 706-707, 2005.

U.S. Appl. No. 10/918,608, filed Sep. 30, 2004, "*Silicone Condensation Reaction*".

U.S. Appl. No. 11/081,070, filed Mar. 15, 2005, "*Disproportionation of Hydridosiloxanes and Crosslinked Polysiloxane Network Derived Therefrom*".

*Primary Examiner*—Elvis O. Price
(74) *Attorney, Agent, or Firm*—Shawn A. McClintic; William E. Powell, III

(57) ABSTRACT

The present invention provides a novel method for the preparation of diorganosilanes by disproportionation of a hydridosiloxanes comprising at least one terminal SiH group and at least one siloxane bond in the presence of Lewis acid catalysts. The reaction is both selective and occurs under mild conditions. The triaryl borane, tris(petafluorophenyl) borane, is especially suited for use as a catalyst in the reaction. Organic catalysts such as tris(pentafluorophenyl) borane are typically preferred owing to their greater solubility and stability in the reaction mixture, relative to inorganic Lewis acid catalysts. The product, diorganosilane may be isolated from the product mixture by conventional techniques such as distillation.

19 Claims, No Drawings

PROCESS FOR SYNTHESIS OF DIORGANOSILANES BY DISPROPORTIONATION OF HYDRIDOSILOXANES

CROSS-REFERENCE TO RELATED APPLICATIONS

This Application claims priority to Polish Patent Application Serial Number P-376014, filed Jun. 30, 2005.

BACKGROUND OF THE INVENTION

The invention relates to a method of preparation of diorganosilanes by disproportionation of a hydridosiloxane comprising at least one terminal SiH group and at least one siloxane bond in the presence of Lewis acid catalysts. The invention also relates to oligosiloxanes that are produced as byproducts of the above reaction.

Two methods that are typically used for synthesis of siloxane oligomers and polymers are ring opening polymerization of cyclic siloxanes and polycondensation. The polycondensation reaction between functional silanes or oligosiloxanes leads to the formation of siloxane bond and elimination of a low molecular weight byproduct. The polycondensation of low molecular weight siloxanol oils is the most common method for synthesis of polysiloxanes that produces water as a byproduct. Other non-hydrolytic condensation reactions can also be used that result in different byproducts (see for example United States Patent Application US2004/0127668 A1). Most of these condensation reactions require the presence of a catalyst. Recently it has been reported that organo-boron compounds are extremely efficient catalysts for the reaction between hydrosilanes and silanols (WO 01/74938 A1) producing hydrogen as a byproduct.

Hydrosilanes and organo-boron compounds are also well known as excellent reducing agents for aldehydes, ketones, esters, imines and other functions. These systems are also able to reduce alcohols in a two-step reaction. First, the silylation of alcohol occurs leading to the formation of alkoxysilane, which in the second step is cleaved producing a hydrocarbon and a disiloxane. The SiOC bond cleavage by silyl hydrides in the presence of Lewis acid catalyst like $B(C_6F5)3$ in many cases occurs quantitatively and so fast that it can be used for the synthesis of polysiloxanes (US2004/0127668 A1). This method of preparation of polysiloxanes may be very attractive as the substrates bearing the SiOR and SiH groups are often commercially available, inexpensive and easy to handle. The byproduct of this condensation is a hydrocarbon and the reaction occurs rapidly under mild conditions.

Diorganosilanes, R1R2SiH2 are typically made by the reduction of dichlorosilanes in the presence of strong reducing agents, which are expensive and very hazardous to handle. These compounds find use in electronic materials, semiconductors, integrated circuits and are useful intermediates for the preparation of novel siloxane and organosilicone copolymers as well as small molecules, such as silahydrocarbons. Dimethylsilane ($Me_2SiH_2$) and trimethylsilane ($Me_3SiH$) are also important substrates for low K dielectric coatings made using chemical vapor deposition (CVD) techniques. Methods for generating diorganosilanes on-demand under safe and convenient conditions are therefore highly desirable.

BRIEF DESCRIPTION OF THE INVENTION

The present invention provides a convenient method for generating diorganosilanes by disproportionation of siloxanes containing at least one SiH bond. In the presence of a Lewis acid catalyst, siloxanes containing SiH bonds underwent a disproportionation reaction that led to the exchange of the hydrogen and siloxane bound at silicon atoms. This scrambling process ultimately produced a product mixture comprising diorganosilanes and higher molecular weight siloxanes.

In one embodiment, the invention relates to a method of making diorganosilane by contacting in a reaction mixture an effective amount of a Lewis acid catalyst with a hydridosiloxane comprising at least one terminal SiH group and at least one siloxane bond, to provide a product mixture comprising at least one diorganosilane, and at least one oligosiloxane.

In another embodiment, the invention relates to a method of making a dialkylsilane, said method comprising the step of contacting in a reaction mixture an effective amount of $B(C_6F_5)_3$ with a hydridosiloxane comprising at least one dialkyl substituted terminal SiH group and at least one siloxane bond.

In a further embodiment, the invention relates to a method of making dimethylsilane, said method comprising the step of contacting in a reaction mixture an effective amount of $B(C_6F_5)_3$ catalyst with a hydridosiloxane comprising at least one dimethyl substituted terminal SiH group and at least one siloxane bond.

Various other features, aspects, and advantages of the present invention will become more apparent with reference to the following description and appended claims.

DETAILED DESCRIPTION OF THE INVENTION

In the following specification and the claims which follow, reference will be made to a number of terms which shall be defined to have the following meanings.

The singular forms "a", "an" and "the" include plural referents unless the context clearly dictates otherwise.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl; difluorovinylidene; trichloromethyl, bromodichloromethyl, bromoethyl, 2-bromotrimethylene (e.g. —CH$_2$CHBrCH$_2$—), and the like. Further examples of aliphatic radicals include allyl, aminocarbonyl (i.e. —CONH$_2$), carbonyl, 2,2-dicyanoisopropylidene (i.e. —CH$_2$C(CN)$_2$CH$_2$—), methyl (i.e. —CH$_3$), methylene (i.e. —CH$_2$—), ethyl, ethylene, formyl (i.e. —CHO), hexyl, hexamethylene, hydroxymethyl (i.e. —CH$_2$OH), mercaptomethyl (i.e. —CH$_2$SH), methylthio (i.e. —SCH$_3$), methylthiomethyl (i.e. —CH$_2$SCH$_3$), methoxy, methoxycarbonyl (i.e. CH$_3$OCO—), nitromethyl (i.e. —CH$_2$NO$_2$), thiocarbonyl, trimethylsilyl (i.e. (CH$_3$)$_3$Si—), t-butyldimethylsilyl, 3-trimethyoxysilylpropyl (i.e. (CH$_3$O)$_3$SiCH$_2$CH$_2$CH$_2$—), vinyl, vinylidene, and the like. By way of further example, a $C_1$–$C_{10}$ aliphatic radical contains at least one but no more than 10 carbon atoms. A methyl group (i.e. CH$_3$—) is an example of a $C_1$ aliphatic radical. A decyl group (i.e. CH$_3$(CH2)$_9$—) is an example of a $C_{10}$ aliphatic radical.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group (C$_6$H$_3$) fused to a nonaromatic component —(CH$_2$)$_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e. —OPhC(CF$_3$)$_2$PhO—), 4-chloromethylphen-1-yl; 3-trifluorovinyl-2-thienyl; 3-trichloromethylphen-1-yl (i.e. 3-CCl$_3$Ph—), 4-(3-bromoprop-1-yl)phen-1-yl (i.e. 4-BrCH$_2$CH$_2$CH$_2$Ph—), and the like. Further examples of aromatic radicals include 4-allyloxyphen-1-oxy, 4-aminophen-1-yl (i.e. 4-H$_2$NPh—), 3-aminocarbonylphen-1-yl (i.e. NH$_2$COPh—), 4-benzoylphen-1-yl, dicyanomethylidenebis(4-phen-1-yloxy) (i.e. —OPhC(CN)$_2$PhO—), 3-methylphen-1-yl, methylenebis(4-phen-1-yloxy) (i.e. —OPhCH$_2$PhO—), 2-ethylphen-1-yl, phenylethenyl, 3-formyl-2-thienyl, 2-hexyl-5-furanyl; hexamethylene-1,6-bis(4-phen-1-yloxy) (i.e. —OPh(CH$_2$)$_6$PhO—); 4-hydroxymethylphen-1-yl (i.e. 4-HOCH$_2$Ph—), 4-mercaptomethylphen-1-yl (i.e. 4-HSCH$_2$Ph—), 4-methylthiophen-1-yl (i.e. 4-CH$_3$SPh—), 3-methoxyphen-1-yl, 2-methoxycarbonylphen-1-yloxy (e.g. methyl salicyl), 2-nitromethylphen-1-yl (i.e. 2-NO$_2$CH$_2$Ph), 3-trimethylsilylphen-1-yl, 4-t-butyldimethylsilylphenl-1-yl, 4-vinylphen-1-yl, vinylidenebis(phenyl), and the like. The term "a $C_3$–$C_{10}$ aromatic radical" includes aromatic radicals containing at least three but no more than 10 carbon atoms. The aromatic radical 1-imidazolyl (C$_3$H$_2$N$_2$—) represents a $C_3$ aromatic radical. The benzyl radical (C$_7$H$_8$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group (C$_6$H$_{11}$CH$_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene2,2-bis (cyclohex-4-yl) (i.e. —C$_6$H$_{10}$C(CF$_3$)$_2$C$_6$H$_{10}$—), 2-chloromethylcyclohex-1-yl; 3-difluoromethylenecyclohex-1-yl; 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. CH$_3$CHBrCH$_2$C$_6$H$_{10}$—), and the like. Further examples of cycloaliphatic radicals include 4-allyloxycyclohex-1-yl, 4-aminocyclohex-1-yl (i.e. H$_2$C$_6$H$_{10}$—), 4-aminocarbonylcyclopent-1-yl (i.e. NH$_2$COC$_5$H$_8$—), 4-acetyloxycyclohex-1-yl, 2,2-dicyanoisopropylidenebis(cyclohex-4-yloxy) (i.e. —OC$_6$H$_{10}$C(CN)$_2$C$_6$H$_{10}$—), 3-methylcyclohex-1-yl, methylenebis(cyclohex-4-yloxy) (i.e. —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl; hexamethylene-1,6-bis(cyclohex-4-yloxy) (i.e. —O C$_6$H$_{10}$(CH$_2$)$_6$C$_6$H$_{10}$O—); 4-hydroxymethylcyclohex-1-yl (i.e. 4-HOCH$_2$C$_6$H$_{10}$—), 4-mercaptomethylcyclohex-1-yl (i.e. 4-HSCH$_2$C$_6$H$_{10}$—), 4-methylthiocyclohex-1-yl (i.e. 4-CH$_3$SC$_6$H$_{10}$—), 4-methoxycyclohex-1-yl, 2-methoxycarbonylcyclohex-1-yloxy (2-CH$_3$OCOC$_6$H$_{10}$O—), 4-nitromethylcyclohex-1-yl (i.e. NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g. (CH$_3$O)$_3$SiCH$_2$CH$_2$C$_6$H$_{10}$—), 4-vinylcyclohexen-1-yl, vinylidenebis(cyclohexyl), and the like. The term "a C$_3$–C$_{10}$ cycloaliphatic radical" includes cycloaliphatic radicals containing at least three but no more than 10 carbon atoms. The cycloaliphatic radical 2-tetrahydrofuranyl (C$_4$H$_7$O—) represents a C$_4$ cycloaliphatic radical. The cyclohexylmethyl radical (C$_6$H$_{11}$CH$_2$—) represents a C$_7$ cycloaliphatic radical.

As noted, the present invention relates to a method of making diorganosilane, said method comprising the step of contacting in a reaction mixture an effective amount of a Lewis acid catalyst with at least one hydridosiloxane comprising at least one terminal SiH group and at least one siloxane bond, to provide a product mixture comprising at least one diorganosilane, and at least one oligosiloxane.

In one embodiment of the present invention, the hydridosiloxane starting material comprises structure (I),

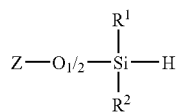

(I)

wherein R$^1$, R$^2$, are independently in each instance a C$_1$–C$_{20}$ aliphatic radical, a C$_3$–C$_{40}$ aromatic radical, or a C$_3$–C$_{40}$ cycloaliphatic radical, and Z is a siloxane moiety represented by structure (II), $$M_aM'_bD_cD'_dT_eT'_fQ_g \qquad (II)$$

wherein the subscripts a, b, c, d, e, f and g are independently zero or a positive integer and wherein M has the formula:

R$^3_3$SiO$_{1/2}$,

M' has the formula:

(Y)R$^4_2$SiO$_{1/2}$,

D has the formula:

R$^5_2$SiO$_{2/2}$,

D' has the formula:

(Y)R$^6$SiO$_{2/2}$,

T has the formula:

R$^7$SiO$_{3/2}$,

T' has the formula:

(Y)SiO$_{3/2}$, and Q has the formula:

SiO$_{4/2}$, wherein R$^3$, R$^4$, R$^5$, R$^6$ and R$^7$ are independently in each instance a C$_1$–C$_{20}$ aliphatic radical, a C$_3$–C$_{40}$ aromatic radical, or a C$_3$–C$_{40}$ cycloaliphatic radical and Y represents a hydrogen.

In one embodiment of the present invention the subscripts a, b, c, d, e, f, and g of structure II are independently a number in a range between 0 and about 1000. In another embodiment of the present invention the subscripts a, b, c, d, e, f, and g of structure II are independently a number in a range between 0 and about 500. In yet another embodiment of the present invention the subscripts a, b, c, d, e, f, and g of structure II are independently a number in a range between 0 and about 100. Thus, by way of example, in one embodiment of the present invention structure II is a polysiloxane moiety, Me$_3$SiO(SiMe$_2$O)$_{500}$—, said polysiloxane moiety having an average chain length of about 500, said polysiloxane moiety comprising a terminal timethylsilyl group. The polysiloxane moiety, Me$_3$SiO(SiMe$_2$O)$_{500}$—, of the foregoing example is represented by structure II wherein the subscript "a" is 1, "b" is zero, "c" is 500, "d" is zero, "e" is zero, "f" is zero, and "g" is zero; and R$^3$ and R$^5$ are methyl (Me) groups.

The product diorganosilane has structure (III),

(III)

wherein R$^1$ and R$^2$ are independently in each instance a C$_1$–C$_{20}$ aliphatic radical, a C$_3$–C$_{40}$ aromatic radical, or a C$_3$–C$_{40}$ cycloaliphatic radical. Typically R$^1$, R$^2$, R$^3$, R$^4$, R$^5$, R$^6$ and R$^7$ groups include, but are not limited to, methyl, ethyl, n-propyl, isopropyl, butyl, pentyl, hexyl, octyl, decyl, dodecyl, 1,1,1-trifluoropropyl, phenyl, naphthyl, benzyl, cyclohexyl, methylcyclohexyl, and the like.

As noted, the method of the present invention requires the use of an appropriate catalyst. In one embodiment, the catalyst is a Lewis acid catalyst. Preferred Lewis acid catalysts include inorganic Lewis acid catalysts such as FeCl$_3$, AlCl$_3$, ZnCl$_2$, ZnBr$_2$, BF$_3$, and the like. The ability of any particular Lewis acid to catalyze the new reaction of the present invention will be a function of acid strength, steric hindrance of both the acid and the substrate and solubility of the Lewis acid and the substrate in the reaction medium. Generally the inorganic Lewis acids, for example, FeCl$_3$, AlCl$_3$, ZnCl$_2$, ZnBr$_2$, BF$_3$, and the like are only sparingly soluble in siloxane materials undergoing the reaction. This low catalyst solubility tends to interfere with the ability of inorganic Lewis acid catalysts to catalyze the desired reaction. Lewis acid catalysts having a greater solubility in siloxane media are more preferred. Thus in one aspect, the present invention employs at least one organic Lewis acid catalyst having formula (IV), $$MR^8_xX_y \qquad (IV)$$

wherein M is selected from the group consisting of B, Al, Ga, In, and Ti; each R$^8$ is independently an aromatic radical having from 5 to 14 carbon atoms, and wherein X is a halogen atom, x is 1, 2, or 3; and y is 0, 1 or 2; with the proviso that x+y=3, and with the further proviso that the catalyst comprise at least one electron withdrawing group. Suitable electron withdrawing groups include halogen atoms, —CF$_3$ groups, —NO$_2$ groups, and —CN groups. The at least one electron withdrawing group may be a functional group forming a part of R$^8$, or the electron withdrawing group may be directly bound to the group M, as is the case when y is 1 or 2. In one embodiment, the catalyst comprises at least one group R$^8$ which is an aromatic radical having from 5 to 14 carbon atoms said group R$^8$ being substituted with at least two halogen atoms.

In another embodiment, the catalyst comprises at least one organic Lewis acid of formula (V), $$BR^8{}_xX_y \quad (V)$$

wherein each $R^8$ is independently an aromatic radical having from 5 to 14 carbon atoms; X is a halogen atom, x is 1, 2, or 3; and y is 0, 1 or 2; with the proviso that x+y=3, and the further proviso that the catalyst comprise at least one electron withdrawing group. Suitable electron withdrawing groups include halogen atoms, —CF$_3$ groups, —NO$_2$ groups, and —CN groups. The at least one electron withdrawing group may be a functional group forming a part of $R^8$, or the electron withdrawing group may be directly bound to the boron group, as is the case when y is 1 or 2 (See for example formulae XII, XIII, XVI, and XVII). In one embodiment, the catalyst comprises at least one group $R^8$ which is an aromatic radical having from 5 to 14 carbon atoms, said group $R^8$ being substituted with at least two halogen atoms. In one embodiment, each $R^8$ is unsubstituted phenyl and X is halogen (See for example, formulae XVI and XVII below). Typical examples of such organic Lewis acid catalysts represented by formula (V) include, but are not limited to:

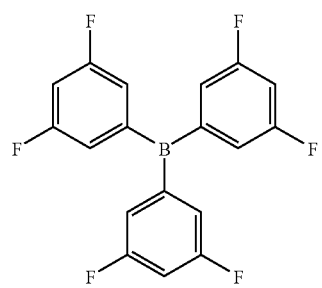 (VI)

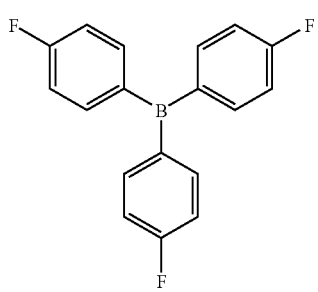 (VII)

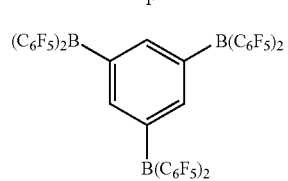 (VIII)

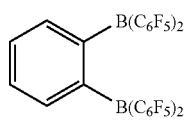 (IX)

(C$_6$F$_4$)(C$_6$F$_5$)$_2$B (X)

(C$_6$F$_4$)$_3$B (XI)

(C$_6$F$_5$)BF$_2$ (XII)

BF(C$_6$F$_5$)$_2$ (XIII)

B(C$_6$F$_5$)$_3$ (XIV)

B(C$_6$H$_5$)(C$_6$F$_5$)$_2$ (XV)

BCl$_2$(C$_6$H$_5$) (XVI)

BCl(C$_6$H$_5$)$_2$ (XVII)

[C$_6$H$_4$(m-CF$_3$)]$_3$B (XVIII)

[C$_6$H$_4$(p-CF$_3$)]$_3$B (XIX)

[C$_6$H$_2$-2,4,6-(CF$_3$)$_3$]$_3$B (XX)

[C$_6$H$_2$-3,4,5-(CF$_3$)$_3$]$_3$B (XXI)

where in structures (X) and (XI), the four fluorine atoms can be substituted either on the 2,3,4,5,6 positions and the remaining carbon valence is substituted by hydrogen.

In one embodiment the present invention relates to a method of making dialkylsilane, said method comprising the step of contacting in a reaction mixture an effective amount of B(C$_6$F$_5$)$_3$ with a hydridosiloxane comprising structure (XXII),

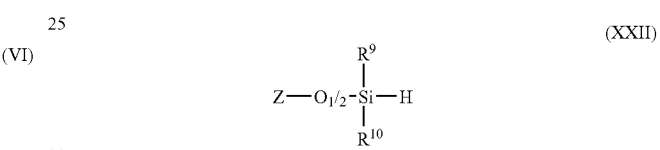 (XXII)

to provide a product mixture comprising at least one dialkylsilane, and at least one oligosiloxane, wherein $R^9$ and $R^{10}$ are independently in each instance a C$_1$–C$_{10}$ alkyl group and Z is a siloxane represented by structure (II). In this embodiment, the product dialkylsilane has structure (XXIII),

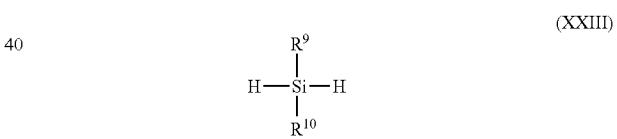 (XXIII)

wherein $R^9$ and $R^{10}$ are independently in each instance a monovalent C$_1$–C$_{10}$ alkyl group.

In a further embodiment the present invention relates to a method of making dimethylsilane, said method comprising the step of contacting in a reaction mixture an effective amount of B(C$_6$F$_5$)$_3$ catalyst with a hydridosiloxane comprising structure (XXIV),

 (XXIV)

wherein Z is a siloxane represented by structure (II).

The catalyst is typically used in an amount in a range of from about 1 to about 50000 ppm by weight based upon a total weight of the reaction mixture, more preferably from about 10 ppm to about 10000 ppm by weight based upon a total weight of the reaction mixture, and most preferably from about 50 ppm to about 5000 ppm by weight based upon a total weight of the reaction mixture.

The reaction may be conducted in the presence of a solvent. Alternatively, the reaction may be conducted in the absence of a solvent. The solvent may be a single solvent or a mixture of solvents. The solvent provides an increased ability to control viscosity of the reaction mixture, and the rate of the reaction, and further provides a convenient means of controlling the exothermicity of the process. Preferred solvents include aliphatic hydrocarbons, aromatic hydrocarbons, halogenated hydrocarbons, as well as oligomeric cyclic diorganosiloxanes that do not comprise Si—H linkages. The reaction may be carried out at room temperature or may be carried out at higher temperatures depending upon such illustrative factors as the chemical structures of the reagents and catalysts, concentration of catalyst and the presence and type of solvent.

The physical state of the diorganosilane compound depends upon such factors as the identities of the substituents on the silicon atoms, temperature, pressure and other prevailing reaction conditions. This product may be isolated and purified, if so desired, by standard methods known to those skilled in the art such as by distillation. Methods to collect and store diorganosilane products are known to those skilled in the art and may be employed in the method of the present invention. The diorganosilane compounds described herein, find use in electronic materials, semiconductors, integrated circuits and are useful intermediates for the preparation of novel siloxane and organosilicone copolymers as well as small molecules, such as silahydrocarbons. The diorganosilane compounds are also important substrates for low K dielectric coating made by CVD process.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLES

In the following examples 1,1,3,3-tetramethylsiloxane was obtained from ABCR and purified and stored over calcium hydride. 1,1,3,3,5,5,7,7-octamethyl-1,3,5,7-tetrasiloxane was obtained from Dr. Chruściel from the Lódź Technical University. The catalyst, tris(pentafluorophenyl) borane ($B(C_6F_5)_3$) obtained from Aldrich Chemical Co., Milwaukee, Wis. was dissolved under dry nitrogen in pre-purified toluene to obtain 0.1 M stock catalyst solution. Reaction products were analyzed using gas chromatography coupled with a mass spectrometer (GC/MS).

Example 1

Oligomerization of 1,1,3,3-tetramethyldisiloxane

In a reaction flask, 0.755 grams (g) (5.62 mmoles) of 1,1,3,3-tetramethyldisiloxane and pre-purified toluene were added using a high vacuum line. Then the flask was filled with dry nitrogen and 0.225 g of dodecane (internal standard for GC analysis) and 0.0124 g (0.024 mmoles) of the catalyst ($B(C_6F_5)_3$) were added using a precision Hamilton syringe under a flow of dry nitrogen. At this point vigorous evolution of gas was observed. Samples were withdrawn at timed intervals, quenched with an excess of 3-ethylpyridine and analyzed by gas chromatography. The assignment of signals was performed by the GC-MS analysis using chemical ionization technique. GC-MS analysis showed that the main products of the reaction were $Me_2SiH_2$, oligomers of the general formula $HMe_2Si(OSiMe_2)_nOSiMe_2H$ where n=1, 2,3 . . . and cyclic siloxanes of series $(Me_2SiO)_n$ where n=3,4 and 5.

Reaction progress, monitored by following the decrease of the substrate concentration proceeded smoothly to almost full conversion of the substrate and produced $Me_2SiH_2$ and $HMe_2Si(OSiMe_2)OSiMe_2H$ as main products. The other products, which were higher oligomers of the $HMe_2Si(OSiMe_2)_nOSiMe_2H$ series, n>1, were formed considerably more slowly than the oligomer n=1. Cyclic products, $D_3$ (hexamethylcyclotrisiloxane) and $D_4$ (octamethylcyclotetrasiloxane) were also produced. A small amount of $D_3$ appeared in the early stages of the reaction but its concentration leveled off. $D_4$ formed slowly but its concentration in the reaction system steadily increased.

Example 2

Reactions of 1,1,3,3,5,5,7,7-octamethyltetrasiloxane

In a reaction flask, 0.980 grams (g) (4.10 mmoles) of 1,1,3,3,5,5,7,7-octamethyltetrasiloxane and pre-purified toluene were added using a high vacuum line. Then the flask was filled with dry nitrogen and 0.225 g of dodecane (internal standard for GC analysis) and 0.0303 g (0.06 mmoles) of the catalyst ($B(C_6F_5)_3$) were added using a precision Hamilton syringe under a flow of dry nitrogen. At this point vigorous evolution of gas was observed. Samples were withdrawn at timed intervals, quenched with an excess of 3-ethylpyridine and analyzed by gas chromatography. The assignment of signals was performed by the GC-MS analysis using chemical ionization technique. GC-MS analysis showed that the main products of the reaction were $Me_2SiH_2$ and hexamethylcyclotrisiloxane, $D_3$.

Reaction progress, monitored by following the decrease of the substrate concentration showed a fast conversion of the substrate initially (57% decrease in less than 1 minute), then the concentration of the substrate showed relatively slow decrease. The main product of the reaction was $D_3$, whose fast increase in concentration corresponded to the fast decrease in the concentration of the substrate. Higher linear and cyclic oligomers were also formed but in very small amounts.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

The invention claimed is:

1. A method of making diorganosilane, said method comprising the step of contacting in a reaction mixture an effective amount of a Lewis acid catalyst with a hydridosiloxane comprising at least one terminal SiH group and at least one siloxane bond, to provide a product mixture comprising at least one diorganosilane, and at least one oligosiloxane.

2. The method of claim 1, wherein said hydridosiloxane comprises structure (I),

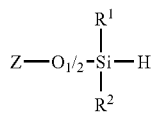 (I)

wherein $R^1$, $R^2$, are independently in each instance a $C_1$–$C_{20}$ aliphatic radical, a $C_3$–$C_{40}$ aromatic radical, or a $C_3$–$C_{40}$ cycloaliphatic radical, and Z is a siloxane represented by structure (II), $$M_a M'_b D_c D'_d T_e T'_f Q_g \quad (II)$$

wherein the subscripts a, b, c, d, e, f and g are zero or a positive integer and wherein M has the formula:

$R^3_3 SiO_{1/2}$,

M' has the formula:

$(Y)R^4_2 SiO_{1/2}$,

D has the formula:

$R^5_2 SiO_{2/2}$,

D' has the formula:

$(Y)R^6 SiO_{2/2}$,

T has the formula:

$R^7 SiO_{3/2}$,

T' has the formula:

$(Y)SiO_{3/2}$, and Q has the formula:

$SiO_{4/2}$, wherein $R^3$, $R^4$, $R^5$, $R^6$ and $R^7$ are independently in each instance a $C_1$–$C_{20}$ aliphatic radical, a $C_3$–$C_{40}$ aromatic radical, or a $C_3$–$C_{40}$ cycloaliphatic radical and Y represents hydrogen.

3. The method of claim 1, wherein said diorganosilane has structure (III),

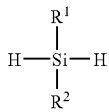 (III)

wherein $R^1$ and $R^2$ are independently in each instance a $C_1$–$C_{20}$ aliphatic radical, a $C_3$–$C_{40}$ aromatic radical, or a $C_3$–$C_{40}$ cycloaliphatic radical.

4. The method of claim 2, wherein at least one of $R^1$, $R^2$, $R^3$, $R^4$, $R^5$, $R^6$ and $R^7$ is selected from the group consisting of methyl, ethyl, n-propyl, isopropyl, butyl, pentyl, hexyl, octyl, decyl, dodecyl, 1,1,1-trifluoropropyl, phenyl, naphthyl, benzyl, cyclohexyl, and methylcyclohexyl.

5. The method of claim 1, wherein the catalyst is used in an amount in a range of from about 1 ppm to about 50000 ppm by weight based on a total weight of the reaction mixture.

6. The method of claim 1, wherein said catalyst has formula (IV), $MR^8_x X_y$ (IV)

wherein M is B, Al, Ga, In or Ti; each $R^8$ is independently an aromatic radical having from 5 to 14 carbon atoms, said catalyst comprising at least one electron-withdrawing group, X is a halogen atom, x is 1, 2, or 3; and y is 0, 1 or 2; with the proviso that x+y=3.

7. The method of claim 6, wherein $R^8$ comprises at least one electron withdrawing moiety selected from the group consisting of halogen, —$CF_3$, —$NO_2$, and —CN.

8. The method of claim 7, wherein $R^8$ comprises at least two halogen atoms.

9. The method of claim 1, wherein said catalyst has formula (V), $BR^8_x X_y$ (V)

wherein each $R^8$ is independently an aromatic radical having from 5 to 14 carbon atoms, said catalyst comprising at least one electron-withdrawing group, X is a halogen atom, x is 1, 2, or 3; and y is 0, 1 or 2; with the proviso that x+y=3.

10. The method of claim 9, wherein $R^8$ comprises at least one electron withdrawing moiety selected from the group consisting of halogen, —$CF_3$, —$NO_2$, and —CN.

11. The method of claim 10, wherein $R^8$ comprises at least two halogen atoms.

12. The method of claim 9, wherein the said catalyst is selected from the group consisting of boron compounds having structures (VI) to (XXI).

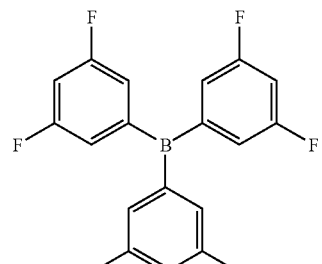 (VI)

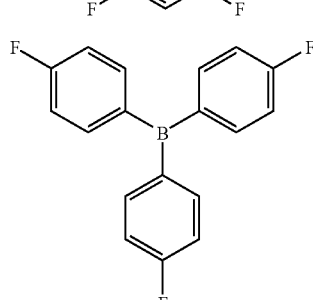 (VII)

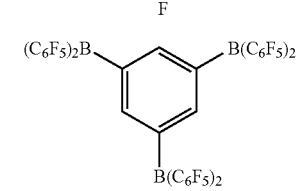 (VIII)

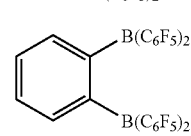 (IX)

$(C_6F_4)(C_6F_5)_2 B$ (X)

$(C_6F_4)_3 B$ (XI)

(C$_6$F$_5$)BF$_2$ (XII)

BF(C$_6$F$_5$)$_2$ (XIII)

B(C$_6$F$_5$)$_3$ (XIV)

B(C$_6$H$_5$)(C$_6$F$_5$)$_2$ (XV)

BCl$_2$(C$_6$H$_5$) (XVI)

BCl(C$_6$H$_5$)$_2$ (XVII)

[C$_6$H$_4$(m-CF$_3$)]$_3$B (XVIII)

[C$_6$H$_4$(p-CF$_3$)]$_3$B (XIX)

[C$_6$H$_2$-2,4,6-(CF$_3$)$_3$]$_3$B (XX)

[C$_6$H$_2$-3,4,5-(CF$_3$)$_3$]$_3$B (XXI)

13. The method of claim 9, wherein the said catalyst is tris(pentafluorophenyl)borane.

14. The method of claim 1, wherein the reaction mixture further comprises at least one solvent.

15. The method of claim 1, wherein said contacting comprises heating at a temperature in a range of from about 0° C. to about 150° C.

16. The method of claim 1, wherein the diorganosilane is isolated from the product mixture by distillation.

17. A method of making dialkylsilane, said method comprising the step of contacting in a reaction mixture an effective amount of B(C$_6$F$_5$)$_3$ with a hydridosiloxane comprising structure (XXII),

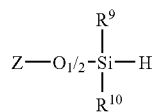

(XXII)

to provide a product mixture comprising at least one dialkylsilane, and at least one oligosiloxane; wherein R$^9$ and R$^{10}$ are independently in each instance a C$_1$–C$_{10}$ alkyl group and Z is a siloxane represented by structure (II), $$M_a M'_b D_c D'_d T_e T'_f Q_g \quad (II)$$

wherein the subscripts a, b, c, d, e, f and g are zero or a positive integer and wherein M has the formula:

R$^3_3$SiO$_{1/2}$,

M' has the formula:

(Y)R$^4_2$SiO$_{1/2}$,

D has the formula:

R$^5_2$SiO$_{2/2}$,

D' has the formula:

(Y)R$^6$SiO$_{2/2}$,

T has the formula:

R$^7$SiO$_{3/2}$,

T' has the formula:

(Y)SiO$_{3/2}$, and Q has the formula:

SiO$_{4/2}$, wherein R$^3$, R$^4$, R$^5$, R$^6$ and R$^7$ are independently in each instance a monovalent C$_1$–C$_{20}$ aliphatic radical, a monovalent C$_3$–C$_{40}$ aromatic radical, or a monovalent C$_3$–C$_{40}$ cycloaliphatic radical and Y represents hydrogen.

18. The method of claim 17, wherein said dialkylsilane has structure (XXIII),

(XXIII)

wherein R$^9$ and R$^{10}$ are independently in each instance a C$_1$–C$_{10}$ alkyl group.

19. A method of making dimethylsilane, said method comprising the step of contacting in a reaction mixture an effective amount of B(C$_6$F$_5$)$_3$ catalyst with a hydridosiloxane comprising structure (XXIV),

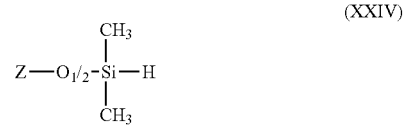

(XXIV)

wherein Z is a siloxane represented by structure (II), $$M_a M'_b D_c D'_d T_e T'_f Q_g \quad (II)$$

wherein the subscripts a, b, c, d, e, f and g are zero or a positive integer and wherein M has the formula:

R$^3_3$SiO$_{1/2}$,

M' has the formula:

(Y)R$^4_2$SiO$_{1/2}$,

D has the formula:

R$^5_2$SiO$_{2/2}$,

D' has the formula:

(Y)R$^6$SiO$_{2/2}$,

T has the formula:

R$^7$SiO$_{3/2}$,

T' has the formula:

(Y)SiO$_{32}$, and Q has the formula:

SiO$_{4/2}$, wherein R$^3$, R$^4$, R$^5$, R$^6$ and R$^7$ are independently in each instance a C$_1$–C$_{20}$ aliphatic radical, a C$_3$–C$_{40}$ aromatic radical, or a C$_3$–C$_{40}$ cycloaliphatic radical and Y represents hydrogen.

* * * * *